United States Patent [19]

Hansen et al.

[11] 4,249,935
[45] Feb. 10, 1981

[54] HERBICIDAL AGENTS

[75] Inventors: Hanspeter Hansen, Ludwigshafen; Karl Eicken, Wachenheim; Bruno Wuerzer, Limburgerhof, all of Fed. Rep. of Germany

[73] Assignee: BASF Aktiengesellschaft, Fed. Rep. of Germany

[21] Appl. No.: 56,949

[22] Filed: Jul. 12, 1979

[51] Int. Cl.³ .............................................. A01N 9/02
[52] U.S. Cl. ........................................... 71/92; 71/95
[58] Field of Search ..................................... 71/92, 95

[56] References Cited

U.S. PATENT DOCUMENTS 4,021,224  5/1977  Pallos et al. ............................. 71/88
4,053,297  10/1977  Richter ................................... 71/90

FOREIGN PATENT DOCUMENTS 1454043  10/1976  United Kingdom.

Primary Examiner—Paul M. Coughlan, Jr.
Attorney, Agent, or Firm—Keil & Witherspoon

[57] ABSTRACT

Herbicidal agents containing at least one substituted anilide of the formula

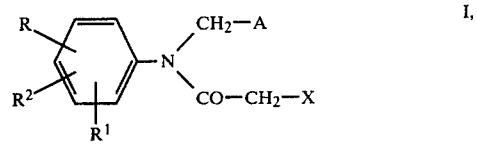

where R denotes hydrogen, linear or branched alkyl or alkoxy of up to 5 carbon atoms, $R^1$ denotes hydrogen, halogen, or linear or branched alkyl or alkoxy of up to 5 carbon atoms, $R^2$ denotes hydrogen, halogen, or linear or branched alkyl or alkoxy of up to 5 carbon atoms, R together with $R^2$ denotes an alkylene chain of up to 6 carbon atoms which is linked in the o-position and may be substituted by linear or branched alkyl of up to 4 carbon atoms, X denotes chlorine or bromine, and A denotes azole which is attached via a ring nitrogen atom and may be mono- or polysubstituted by halogen, phenyl, alkyl, alkoxy, alkylthio or perfluoroalkyl, each of up to 4 carbon atoms, cyano, carboxy, carbalkoxy of up to 4 carbon atoms in the alkoxy, or alkanoyl of up to 4 carbon atoms, or A denotes a salt of an azole containing 2 or 3 nitrogen atoms, as herbicidal active ingredient, and N-dichloroacetyl-2,2-dimethyl-1,3-oxazolidine as antagonistic agent.

The ratio of acetanilide to N-dichloroacetyl-2,2-dimethyl-1,3-oxazolidine is, whether they are applied separately or together, from 1:2 to 1:0.01 parts by weight.

9 Claims, No Drawings

HERBICIDAL AGENTS

The present invention relates to herbicidal agents containing substituted acetanilides as herbicidal active ingredients and N-dichloroacetyl-2,2-dimethyl-1,3-oxazolidine as antagonistic agent, and a process for the selective control of unwanted plant growth with these herbicidal agents.

Substituted acetanilides of the formula

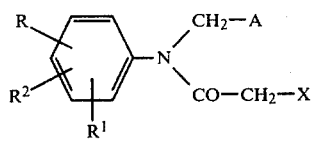

where R denotes hydrogen, linear or branched alkyl or alkoxy of up to 5 carbon atoms, $R^1$ denotes hydrogen, halogen, or linear or branched alkyl or alkoxy of up to 5 carbon atoms, $R^2$ denotes hydrogen, halogen, or linear or branched alkyl or alkoxy of up to 5 carbon atoms, R together with $R^2$ denotes an alkylene chain of up to 6 carbon atoms which is linked in the o-position and may be substituted by linear or branched alkyl of up to 4 carbon atoms, X denotes chlorine or bromine, and A denotes azole which is attached via a ring nitrogen atom and may be mono- or polysubstituted by halogen, phenyl, alkyl, alkoxy, alkylthio or perfluoroalkyl, each of up to 4 carbon atoms, cyano, carboxy, carbalkoxy of up to 4 carbon atoms in the alkoxy, or alkanoyl of up to 4 carbon atoms, or A denotes a salt of an azole containing 2 or 3 nitrogen atoms, have an excellent herbicidal action, but cause damage to crops such as Indian corn and Gramineae.

It was therefore the object of the invention to provide antagonistic agents which offset this poor tolerance of herbicidal acetanilides by certain crop plants.

Antagonistic agents (antidotes) are chemical compounds as a result of the presence of which the tolerance, by certain crop plants, of non-selective or insufficiently selective herbicidal active ingredients is increased without their action on unwanted plants being impaired.

Herbicidal agents containing, in addition to chloroacetanilides as herbicidal active ingredients, antagonistic dichloroacetamides have been disclosed in U.S. Pat. No. 4,053,297 and German Laid-Open Applications DE-OS Nos. 2,218,097 and 2,402,983. Dichloroacetamides in which the 2 substituents on the nitrogen atom form, with it, a heterocyclic ring which may contain a further hetero atom and is unsubstituted or substituted by alkyl are mentioned inter alia in these publications as possible antidotes. N-dichloroacetyl-2,2-dimethyl-1,3-oxazolidine is given as an example of this class of compounds.

However, German Laid-Open Application DE-OS No. 2,218,097 only recommends this antagonistic compound in combination with herbicidally active thiolcarbamates, whereas it is known from German Laid-Open Application DE-OS No. 2,402,983 and U.S. Pat. No. 4,053,297 that N-dichloroacetyl-2,2-dimethyl-1,3-oxazolidine is suitable as an antidote for reducing damage caused to Indian corn by herbicidally active chloroacetanilides. In addition to the chloroacetyl group, these chloroacetanilides bear on the nitrogen substituted alkyl, alkoxyalkyl, alkenyloxyalkyl or cycloalkyloxyalkyl radicals or oxygen- and/or sulfur-containing saturated rings attached via a methylene group.

We have now found that N-dichloroacetyl-2,2-dimethyl-1,3-oxazolidone is suitable for increasing the tolerance by crop plants of herbicidal substituted acetanilides of the formula I. Herbicidal agents containing at least one substituted acetanilide of the formula I and N-dichloroacetyl-2,2-dimethyl-1,3-oxazolidine may be employed without difficulty in Indian corn. The good herbicidal action of the acetanilides is unimpaired, and damage to the crop plants is eliminated.

Acetanilides whose tolerance by crop plants can be increased by N-dichloroacetyl-2,2-dimethyl-1,3-oxazolidine are those of the formula I in which R is hydrogen, alkyl of a maximum of 5 carbon atoms, such as methyl, ethyl, n-propyl, isopropyl, n-butyl, sec-butyl, isobutyl, tert-butyl, linear and branched pentyl, and alkoxy of a maximum of 5 carbon atoms, such as methoxy, ethoxy, propoxy, butoxy and pentoxy;

$R^1$ and $R^2$ are hydrogen, halogen, such as fluorine, chlorine, bromine and iodine, alkyl of a maximum of 5 carbon atoms, such as methyl, ethyl, n-propyl, isopropyl, n-butyl, sec-butyl, isobutyl, tert-butyl, linear and branched pentyl, and alkoxy of a maximum of 5 carbon atoms, such as methoxy, ethoxy, propoxy, butoxy, and pentoxy;

$R^2$ together with R is an alkylene chain of a maximum of 6 carbon atoms, linked in the o-position and unsubstituted or substituted by alkyl of a maximum of 4 carbon atoms, e.g., ethylene, trimethylene, tetramethylene, 1-methyltrimethylene, 1,1-dimethyltrimethylene, and 1,1-dimethyltetramethylene;

X is chlorine, bromine or iodine, preferably chlorine;

A is an azole attached via a ring nitrogen atom, e.g., pyrrole, pyrazole, imidazole, 1,2,4-triazole, 1,2,3-triazole, and tetrazole, which be mono- or polysubstituted by halogen, phenyl, alkyl, alkoxy, alkylthio or perfluoroalkyl, each of up to 4 carbon atoms, cyano, carboxy, or carbalkoxy with up to 4 carbon atoms in the alkoxy, or alkanoyl of up to 4 carbon atoms, the substituents being identical or different, such as 2,6-dimethylpyrrole, tetramethylpyrrole, 3(5)-methylpyrazole, 4-methylpyrazole, 3(5)-ethylpyrazole, 4-ethylpyrazole, 3(5)-isopropylpyrazole, 4-isopropylpyrazole, 3,5-dimethylpyrazole, 3,5-dimethyl-4-acetylpyrazole, 3,5-dimethyl-4-propionylpyrazole, 3,4,5-trimethylpyrazole, 3(5)-phenylpyrazole, 4-phenylpyrazole, 3,5-diphenylpyrazole, 3(5)-phenyl-5(3)-methylpyrazole, 3(5)-chloropyrazole, 4-chloropyrazole, 4-bromopyrazole, 4-iodopyrazole, 3,4,5-trichloropyrazole, 3,4,5-tribromopyrazole, 3,5-dimethyl-4-chloropyrazole, 3,5-dimethyl-4-bromopyrazole, 4-chloro-3(5)-methylpyrazole, 4-bromo-3(5)-methylpyrazole, 4-methyl-3,5-dichloropyrazole, 3(5)-methyl-4,5(3)-dichloropyrazole, 3(5)-chloro-5(3)-methylpyrazole, 4-methoxypyrazole, 3(5)-methyl-5(3)-methoxypyrazole, 3(5)-ethoxy-4,5(3)-dimethylpyrazole, 3(5)-methyl-5(3)-trifluoromethylpyrazole, 3,5-bis-trifluoromethylpyrazole, 3(5)-methyl-5(3)-carbethoxypyrazole, 3,5-bis-carbethoxypyrazole, 3,4,5-triscarbethoxypyrazole, 3(5)-methyl-5(3)-methylthio-4-carbethoxypyrazole, 4-methyl-3,5-biscarbethoxypyrazole, 4-cyanopyrazole, 4-methoxy-3,5-dichloropyrazole, 4,5-dichloroimidazole, 2-ethyl-4,5-dichloroimidazole, 2-methyl-4,5-dichloroimidazole, 3(5)-methyl-1,2,4-triazole, 3,5-dimethyl-1,2,4-triazole, 3(5)-chloro-1,2,4-triazole, 3(5)-bromo-1,2,4-triazole, 3(5)-chloro-5(3)-methyl-1,2,4-triazole, 3,5-dichloro-1,2,4-triazole, 3,5-dibromo-1,2,4-triazole, 3(5)-chloro- 5(3)-cyano-1,2,4-triazole, 3(5)-chloro-5(3)-phenyl-1,2,4-triazole, 3(5)-chloro-5(3)-carbomethoxy-1,2,4-triazole, 3(5)-methylthio-1,2,4-triazole, 4(5)-methyl-1,2,3-triazole, 4,5-dimethyl-1,2,3-triazole, 4(5)-phenyl-1,2,3-triazole, 4(5)-chloro-1,2,3-triazole, 1,2,3-triazol-4(5)-yl-carboxylic acid ethyl ester, 1,2,3-triazol-4,5-yl-dicarboxylic acid dimethyl ester, 5-methyltetrazole, 5-chlorotetrazole, and tetrazolyl-5-carboxylic acid ethyl ester.

Furthermore, the radical A may, when the optionally substituted azole contains 2 or 3 nitrogen atoms, also be attached in a salt-like manner to one of the usual strong inorganic or organic acids, e.g., hydrochloric acid, hydrobromic acid, nitric acid, sulfuric acid, tetrafluoboric acid, fluosulfonic acid, and formic acid, a halogenated carboxylic acid, e.g., trichloroacetic acid, an alkanesulfonic acid, e.g., methaneulfonic acid, a halogenated alkanesulfonic acid, e.g., trifluoromethanesulfonic acid and perfluorohexanesulfonic acid, and an arylsulfonic acid, e.g. dodecylbenzenesulfonic acid.

Preferred acetanilides are those which bear methyl or ethyl in the 2- and 6-positions on the phenyl ring and hydrogen, methyl or ethyl in the 3-position; suitable azoles are pyrazole, imidazole, triazole and tetrazole, which are unsubstituted or substituted by lower alkyl, alkoxy, carbalkoxy, cyano or halogen.

In particular, the herbicidal agents according to the invention contain the following acetanilides:
2-chloro-2',6'-dimethyl-N-(pyrazol-1-yl-methyl)-acetanilide, 2-chloro-2'-methyl-6'-ethyl-N-(pyrazol-1-yl-methyl)-acetanilide, 2-chloro-2',6'-dimethyl-N-(4-methylpyrazol-1-yl-methyl)-acetanilide, 2-chloro-2'-methyl-6'-ethyl-N-(4-methoxypyrazol-1-yl-methyl)-acetanilide, 2-chloro-2'-methyl-6'-ethyl-N-(3(5)-methyl-pyrazol-1-yl)-acetanilide, 2-chloro-2', 6'-dimethyl-N-(3,5-dimethylpyrazol-1-yl-methyl)-acetanilide, 2-chloro-2',6'-dimethyl-N-(1,2,4-triazol-1-yl-methyl)-acetanilide, 2-chloro-2',6'-dimethyl-N-(4-chloropyrazol-1-yl-methyl)-acetanilide, 2-chloro-2',3',6'-trimethyl-N-(pyrazol-1-yl-methyl)-acetanilide, 2-chloro-2'-methyl-6'-ethyl-N-(3,5-dimethylpyrazol-1-yl-methyl)-acetanilide, 2-chloro-2',6'-diethyl-N-(3,5-dimethylpyrazol-1-yl-methyl)-acetanilide, 2-chloro-2',3',6'-trimethyl-N-(3,5-dimethylpyrazol-1-yl-methyl)-acetanilide, 2-chloro-2',6'-diethyl-N-(4-methylpyrazol-1-yl-methyl)-acetanilide, 2-chloro-2'-methyl-6'-ethyl-N-(4-methylpyrazol-1-ylmethyl)-acetanilide, 2-chloro-2',3',6'-trimethyl-N-(4-methylpyrazol-1-yl-methyl)-acetanilide, 2-chloro-2',6'-dimethyl-N-(3-(5)-methyl-pyrazol-1-yl-methyl)-acetanilide, 2-chloro-2',6'-diethyl-N-(3-(5)-methylpyrazol-1-yl-methyl)-acetanilide, 2-chloro-2',6'-dimethyl-N-(4-methoxypyrazol-1-yl-methyl)-acetanilide, 2-chloro-2',6'-diethyl-N-(pyrazol-1-yl-methyl)-acetanilide, 2-chloro-2',6'-dimethyl-N-(4,5-dichloroimidazol-1-yl-methyl)-acetanilide, 2-chloro-2'-methyl-6'-ethyl-N-(4,5-dichloroimidazol-1-yl-methyl)-acetanilide, 2-chloro-2'-methyl-6'-ethyl-N-(2-ethyl-4,5-dichloroimidazol-1-yl-methyl)-acetanilide, 2-chloro-2',6'-diethyl-N-(4,5-dichloroimidazol-1-yl-methyl)-acetanilide, 2-chloro-2'-methyl-6'-ethyl-N-(1,2,4-triazol-1-yl-methyl)-acetanilide, 2-chloro-2',6'-diethyl-N-(1,2,4-triazol-1-yl-methyl)-acetanilide and 2-chloro-2',3',6'-trimethyl-N-(1,2,4-triazol-1-yl-methyl)-acetanilide.

A particularly preferred agent according to the invention contains, in addition to N-dichloroacetyl-2,2-dimethyl-1,3-oxazolidine, 2-chloro-2',6'-dimethyl-N-(pyrazol-1-yl-methyl)-acetanilide as herbicidal active ingredient.

The acetanilides of the formula I are disclosed in German Laid-Open Applications DE-OS Nos. 2,648,008 and 2,744,396. They may be obtained by reaction of 2-halo-N-halomethylacetanilides of the formula II with a 1H-azole of the formula H—A in accordance with the following equation:

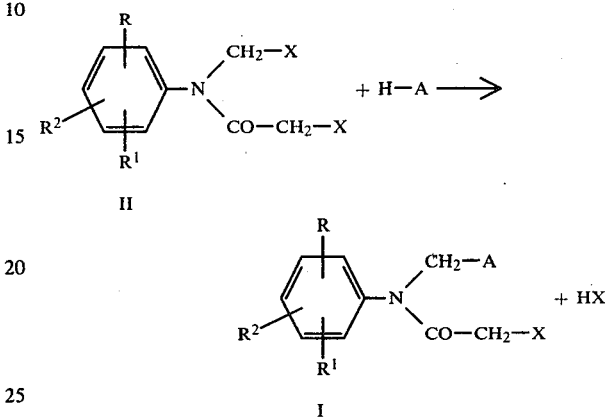

R, $R^1$, $R^2$ and X have the above meanings and A denotes an azole linked via a ring nitrogen atom and which may be mono- or polysubstituted by halogen, phenyl, alkyl, alkoxy, alkylthio or perfluoroalkyl, each of up to 4 carbon atoms, cyano, carboxy, carbalkoxy of up to 4 carbon atoms in the alkoxy, or alkanoyl of up to 4 carbon atoms.

The manufacture of N-dichloroacetyl-2,2-dimethyl-1,3-oxazolidine is disclosed in German Laid-Open Applications DE-OS Nos. 2,218,097 and 2,402,983.

N-dichloroacetyl-2,2-dimethyl-1,3-oxazolidine itself has scarcely any influence, if at all, on the germination and growth of crop and unwanted plants, even at application rates well above those required for an antagonistic effect. However, it is capable of considerably reducing the phytotoxicity of the herbicidal acetanilides of the formula I to crop plants such as Indian corn, or of eliminating it completely.

In these case of herbicidal acetanilides which are less aggressive to crop plants, low additions of N-dichloroacetyl-2,2-dimethyl-1,3-oxazolidine are sufficient. The ratio of acetanilide to N-dichloroacetyl-2,2-dimethyl-1,3-oxazolidine may vary within wide limits, and depends on the acetanilide. Suitable ratios of herbicidal active ingredient to N-dichloroacetyl-2,2-dimethyl-1,3-oxazolidine are from 1:2 to 1:0.01 parts by weight.

Acetanilides and antagonistic compounds may be incorporated into the soil either together or separately and before or after sowing. With acetanilides of the formula I, the commonest method is to apply them to the surface of the soil immediately after sowing, or in the period between sowing and emergence of the young plants. It is also possible to apply them during emergence and shortly thereafter. In each instance, the antagonistic agent may be applied simultaneously with the herbicidal active ingredient. It is also possible to apply the compounds separately—either the antagonist first and then the herbicidal active ingredient, or vice versa—provided that, if the herbicidal active ingredient is applied first, not too much time elapses before the antagonist is applied as otherwise the crop plants may be damaged. The active ingredient and antagonist may be suspended, emulsified or dissolved in a spray liquor or may be in granular form, and may be formulated together or separately. It is also feasible to treat the seed with the antagonist before sowing. The herbicidal active ingredient is then applied on its own in the usual manner.

The novel herbicidal agents may contain, in addition to acetanilide and N-dichloroacetyl-2,2-dimethyl-1,3-oxazolidine, other herbicidal or growth-regulating active ingredients of different chemical structure, e.g., 2-chloro-4-ethylamino-6-isopropylamino-1,3,5-triazine, without the antagonistic effect being impaired.

The agents according to the invention, or, when applied separately, the herbicidal active ingredients and the antidote are applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure very fine distribution of the agents according to the invention or their individual components.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the herbicidal active ingredient and/or antidote, as such or dissolved in an oil or solvent, may be homogenized in water by means of wetting or dispersing agents, adherents or emulsifiers. Concentrates which are suitable for dilution with water may be prepared from herbicidal active ingredient and/or antidote, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the herbicidal active ingredient and/or antidote with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of herbicidal active ingredient and/or antidote. Application rates are from 0.2 to 5 kg of herbicidal active ingredient per hectare. This amount of herbicidal active ingredient is applied, together or separately, with such an amount of antidote to give a ratio of herbicidal active ingredient to antagonist of from 1:2 to 1:0.01 parts by weight.

Examples of formulations are given below.

I. 40 parts by weight of a mixture of 4 parts by weight of 2-chloro-2',6'-dimethyl-N-(pyrazol-1-yl-methyl)-acetamide and 1 part by weight of N-dichloroacetyl-2,2-dimethyl-1,3-oxazolidine is intimately mixed with 10 parts of the sodium salt of a phenosulfonic acid-urea-formaldehyde condensate, 2 parts of silica gel and 48 parts of water. A stable, aqueous dispersion is obtained. Dilution in 100,000 parts by weight of water gives an aqueous dispersion containing 0.04 wt% of the mixture of active ingredient + antidote.

II. 3 parts by weight of a mixture of 1 part by weight of 2-chloro-2',6'-dimethyl-N-(pyrazol-1-yl-methyl)-acetanilide and 1 part by weight of N-dichloroacetyl-2,2-dimethyl-1,3-oxazolidine is intimately mixed with 97 parts by weight of particulate kaolin. A dust is obtained containing 3% by weight of the mixture of active ingredient + antidote.

III. 30 parts by weight of a mixture of 1 part by weight of 2-chloro-2'-methyl-6'-ethyl-N-(1,2,4-triazol-1-yl-methyl)-acetanilide and 1 part by weight of N-dichloroacetyl-2,2-dimethyl-1,3-oxazolidine is intimately mixed with a mixture consisting of 92 parts by weight of powdered silica gel and 8 parts by weight of paraffin oil which has been sprayed onto the surface of this silica gel. A formulation is obtained having good adherence.

IV. 20 parts by weight of a mixture of 8 parts by weight of 2-chloro-2'-methyl-6'-ethyl-N-(pyrazol-1-yl-methyl)-acetanilide and 1 part by weight of N-dichloroacetyl-2,2-dimethyl-1,3-oxazolidine is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

V. 20 parts by weight of a mixture of 10 parts by weight of 2-chloro-2',6'-dimethyl-N-(4,5-dichloroimidazol-1-yl-methyl)-acetanilide and 1 part by weight of N-dichloroacetyl-2,2-dimethyl-1,3-oxazolidine is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and finely distributing it therein, an aqueous dispersion is obtained containing 0.02% by weight of the mixture of active ingredient-+antidote.

Greenhouse experiments show that the use of the herbicidal agents according to the invention increases the tolerance of the herbicidal acetanilides by the crop plants without the herbicidal action being affected.

Plastic boxes 51 cm long, 32 cm wide and 6 cm deep were filled with loamy sand (pH: 6 to 7) containing about 1.5% humus. Indian corn (Zea mays) was sown shallow, in rows, in this substrate. Echinochloa crus-galli was scattered at random an unwanted plant. The non-sterilized soil also additionally contained viable weed seeds which contributed to the weed population. A field with crop plants growing in it and infested with weeds was thus simulated.

The active ingredients and the antagonist were applied separately and in the mixtures given below. They were emulsified or suspended in water as vehicle and the liquor was sprayed through finely distributing nozzles onto the soil surface, either immediately after sowing or prior to emergence of the test plants. After sowing and treatment the boxes were sprinkler-irrigated and covered with transparent plastic hoods until the plants emerged. These measures ensured that the plants germinated and took root uniformly. The boxes were set up in the greenhouse at from 18° to 30° C. These greenhouse experiments were monitored until 3 to 5 Indian corn leaves had developed.

The scale for assessing the action of the agents was 0 to 100, 0 denoting normal emergence and development of the plants, with reference to the untreated control, and 100 denoting non-germination or withering of the plants. It should be borne in mind here that, for instance in Indian corn, odd crippled or retarded plants may occur even under completely normal conditions and without any chemical treatment.

The following table shows the extent to which N-dichloroacetyl-2,2-dimethyl-1,3-oxazolidine increases the tolerance by Indian corn of acetanilides of the formula I, e.g., 2-chloro-2',6'-dimethyl-N-(pyrazol-1-yl-methyl)-acetanilide.

TABLE

Improvement in the tolerance by Indian corn of 2-chloro-2',6'-dimethyl-N-(pyrazol-1-yl-methyl)-acetanilide by means of N-dichloroacetyl-2,2-dimethyl-1,3-oxazolidine; preemergence treatment in the greenhouse

| Herbicidal active ingredient | Antagonistic compound | Appln. rate [kg/ha] | Zea mays | Echinochloa crus galli |
|---|---|---|---|---|
| 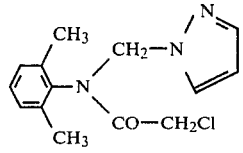 A | — | 1.0 | 64 | 99 |
| | | 2.0 | 79 | 99 |
| | 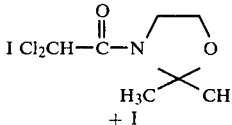 I | 4.0 | 2 | 0 |
| A | + I | 1.0 + 0.25 | 15 | 98 |
| | | 1.0 + 2.0 | 10 | 98 |
| | | 2.0 + 0.5 | 14 | 99 |
| | | 2.0 + 2.0 | 10 | 100 |

0 = normal emergence, no damage
100 = non-emergence, or plants withered

We claim:

1. A herbicidal agent containing a herbicidally effective amount of a substituted acetanilide of the formula

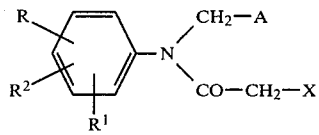

where R denotes hydrogen, linear or branched alkyl or alkoxy of up to 5 carbon atoms, $R^1$ denotes hydrogen, halogen, or linear or branched alkyl or alkoxy of up to 5 carbon atoms, $R^2$ denotes hydrogen, halogen, or linear or branched alkyl or alkoxy of up to 5 carbon atoms, R together with $R^2$ denotes an alkylene chain of up to 6 carbon atoms which is linked in the o-position and may be substituted by linear or branched alkyl of up to 4 carbon atoms, X denotes chlorine or bromine, and A denotes azole selected from the group consisting of pyrrole, pyrazole, imidazole, 1,2,4-triazole, 1,2,3-triazole and tetrazole, which is attached via a ring nitrogen atom and may be mono- or polysubstituted by halogen, phenyl, alkyl, alkoxy, alkylthio or perfluoroalkyl, each of up to 4 carbon atoms, cyano, carboxy, carbalkoxy of up to 4 carbon atoms in the alkoxy, or alkanoyl of up to 4 carbon atoms, or A denotes a salt of one of said unsubstituted or substituted azoles containing 2 or 3 nitrogen atoms and an antidotally effective amount of N-dichloroacetyl-2,2-dimethyl-1,3-oxazolidine, the ratio of acetanilide to N-dichloroacetyl-2,2-dimethyl-1,3-oxazolidine is from 1:2 to 1:0.01 parts by weight.

2. A herbicidal agent as set forth in claim 1, wherein the substituted acetanilide is 2-chloro-2'-6'-dimethyl-N-(pyrazol-1-yl-methyl)-acetanilide.

3. A herbicidal agent as set forth in claim 1, wherein the ratio of acetanilide to N-dichloroacetyl-2,2-dimethyl-1,3-oxazolidine is from 1:2 to 10:1 parts by weight.

4. A method of controlling unwanted plant growth and protecting crop plants, comprising applying to the plants and their habitat a herbicidally effective amount of an acetanilide of the formula I as set forth in claim 1, and an antidotally effective amount of N-dichloroacetyl-2,2-dimethyl-1,3-oxazolidine.

5. A method of protecting crop plants from injury due to a herbicidal acetanilide of the formula I as set forth in claim 1, comprising applying to the soil, after sowing of the crop seed, a herbicidal agent comprising a herbicidally effective amount of said acetanilide and an antidotally effective amount of N-dichloroacetyl-2,2-dimethyl-1,3-oxazolidine.

6. A method of protecting crop plants from injury due to a herbicidal acetanilide of the formula I as set forth in claim 1 comprising applying to the soil in which a herbicidally effective amount of said acetanilide is used, an antidotally effective amount of N-dichloroacetyl-2,2-dimethyl-1,3-oxazolidine.

7. A method of protecting Indian corn plants from injury due to a herbicidal acetanilide of the formula I as set forth in claim 1 comprising applying to the soil in which a herbicidally effective amount of said acetanilide is used, an antidotally effective amount of N-dichloroacetyl-2,2-dimethyl-1,3-oxazolidine.

8. A method of protecting a crop from injury due to a herbicidal acetanilide of the formula I as set forth in claim 1 comprising applying to the crop seed, prior to sowing, an antidotally effective amount of N-dichloroacetyl-2,2-dimethyl-1,3-oxazolidine.

9. The method of claims 4, 5, 6, 7 or 8 wherein the ratio of acetanilide to N-dichloroacetyl-2,2-dimethyl-1,3-oxazolidine is from 1:2 to 10:1 parts by weight.

* * * * *